US006821780B2

(12) United States Patent
Thorel et al.

(10) Patent No.: US 6,821,780 B2
(45) Date of Patent: Nov. 23, 2004

(54) COMPLETE NUTRIENT MEDIUM FOR USE AS A COSMETIC AND COSMETIC USE THEREOF

(75) Inventors: Jean-Noel Thorel, 3 rue la Rochelle, F-75014 Paris (FR); Hugues Gatto, Albertville (FR)

(73) Assignee: Jean-Noel Thorel, Paris (FR)

( * ) Notice: Subject to any disclaimer, the term of this patent is extended or adjusted under 35 U.S.C. 154(b) by 0 days.

(21) Appl. No.: 08/860,231

(22) PCT Filed: Jan. 9, 1996

(86) PCT No.: PCT/FR96/00037

§ 371 (c)(1),
(2), (4) Date: Jul. 25, 1997

(87) PCT Pub. No.: WO96/21421

PCT Pub. Date: Jul. 18, 1996

(65) Prior Publication Data

US 2002/0034499 A1 Mar. 21, 2002

(30) Foreign Application Priority Data

Jan. 9, 1995 (FR) ............................................. 95 00329
Jan. 9, 1995 (FR) ............................................. 95 00327

(51) Int. Cl.⁷ ................................................. C12N 5/00
(52) U.S. Cl. ........................ 435/404; 435/325; 435/405
(58) Field of Search ................................ 435/325, 371, 435/404, 405, 374; 514/2, 21

(56) References Cited

U.S. PATENT DOCUMENTS 4,385,049 A * 5/1983 Cuca .......................... 424/167
5,292,655 A * 3/1994 Wille, Jr. .................. 435/240.2
5,461,030 A * 10/1995 Lindenbaum ................... 544/4
5,591,709 A * 1/1997 Lindenbaum ................... 514/4
5,686,307 A * 11/1997 Wille, Jr. ..................... 435/405

FOREIGN PATENT DOCUMENTS

| DE | 4139639 | * | 6/1993 |
| FR | 2694692 | | 2/1994 |
| JP | 62-19511 | | 1/1987 |
| WO | WO 94/13260 | | 6/1994 |

OTHER PUBLICATIONS

S. Boyce et al., Calcium–Regulated Differentiation of Normal Human Epidermal Keratinocytes in Chemically Defined Clonal Culture and Serum–Free Serial Culture; *Journal of Investigative Dermatology*, vol. 81, No. 1, pp. 33s–40s, (1983).
S. Boyce et al., Cultivation, Frozen Storage, and Clonal Growth of Normal Human Epidermal Keratinocytes in Serum–Free Media; *Journal of Tissue Culture Methods*, vol. 9, No. 2, pp. 83–93, (1985).

* cited by examiner

*Primary Examiner*—Jean C. Witz
(74) *Attorney, Agent, or Firm*—Oliff & Berridge, PLC

(57) ABSTRACT

A complex nutrient medium containing compounds that are biocompatible, biomimetic and bioavailable in the skin, but no biological extract of animal or cellular origin, for preparing a topical composition. Said complex nutrient medium has a suitable composition enabling viable in vitro culture of a human epidermal keratinocyte inoculum, with at least one clonal proliferation thereof during the first stage, and without the use of a live nutritive layer. The composition may be used as the active principle, particularly in a cosmetic preparation or a galenic base, and as a carrier capable of potentiating the activity of specific active principles.

2 Claims, 3 Drawing Sheets

A

B

C

COMPLETE NUTRIENT MEDIUM FOR USE AS A COSMETIC AND COSMETIC USE THEREOF

Figure 1:

The present invention relates to a complex nutrient medium, to its applications and more especially to its use for manufacturing a composition for topical use, and in particular for topical cosmetic or medicinal use.

The composition obtained according to the invention enables an extracellular environment which is entirely suited to the epidermis to be obtained, by supplying in particular:

an optimized nutritional provision, both other components in respect of vitamins, trace elements and and pH and osmolarity characteristics close to physiological conditions.

Generally speaking, according to the invention, the nutritional agent consists of a complex nutrient medium comprising compounds which are both biocompatible, biomimetic and bioavailable in respect of the skin, excluding any biological extract of animal origin, such as foetal calf serum, or of cellular origin.

The complex nutrient medium adopted according to the invention has a composition suitable for permitting, on its own and in an aqueous medium, viable in vitro culture of an inoculum of human epidermal keratinocytes, with at least one clonal proliferation of the latter at the first passage, without a living nourishing substrate such as fibroblasts.

"Biocompatible" is understood to mean the property according to which the compound is harmless to the skin.

"Biomimetic" is understood to mean the fact that the compound is present in the natural state in the skin.

"Bioavailable" is understood to mean the property according to which the compound is assimilable by human epidermal keratinocytes, both in vitro and in vivo.

By routine tests, a person skilled in the art is in a position to formulate a complex nutrient medium according to the invention, in particular by carrying out with the said medium in vitro culturing of keratinocytes, the growth of which can be observed, for example under a microscope.

In this connection, the following documents have already described media suited to in vitro culturing of keratinocytes, the viability and growth of which can be determined by the tests currently in use, and be directly assessed by observation under a microscope:

Boyce ST, Ham RG, Calcium-regulated differentiation of normal human epidermal keratinocytes in defined clonal culture and serum-free serial culture, J. Invest. Dermatol. 1983; 81: 33S–40S Boyce S T, Ham R G, Cultivation, frozen storage, and clonal growth of normal human epidermal keratinocytes in serum-free media, J. Tissue Culture Methods. 1985; 9: 83–93.

Where necessary, the content of these publications is incorporated in the present description.

The complex nutrient medium according to the invention comprises amino acids, one or more vitamins, one or more organic components and one or more inorganic salts.

A composition of the invention for topical use comprises a phase which is biocompatible with the superficial parts of the human body, in which phase at least the said nutrient medium as defined above is distributed homogeneously.

In a composition according to the present invention, the biocompatible phase in which the nutritional agent is distributed can constitute the excipient, or one of the components of the excipient, of the said composition.

Since all of the compounds present in the nutrient medium according to the invention are water-soluble, two methods of formulation may be employed in order to obtain a composition for topical use:

1) Aqueous continuous phase, containing the nutrient medium according to the invention:

in the form of an aqueous gel, with the aid of a nonionic water-soluble polymer of the polysaccharide or cellulose ether type (polymers compatible with the high ionic strength of the medium);

in the form of an emulsified system (oil-in-water emulsion employing surfactants that withstand high ionic strengths);

in the form of a cosmetic serum.

2) Oily continuous phase, the discontinuous phase containing the nutrient medium according to the invention:

in emulsified form, on the understanding that the ionic strength of the discontinuous phase entails instability of the emulsion; it is, however, possible to formulate lamellar or cylindrical phases having better stability, or alternatively a two-phase system re-emulsified immediately before use by simple shaking;

by encapsulation:

in a rigid capsule of the polysaccharide type, dispersed in the lipid phase, in a soft capsule of the gelatin type, dispersed in the discontinuous phase.

The use of liposomes as an encapsulation delivery agent can be envisaged in the form of a liposomal gel in an aqueous continuous phase.

A composition according to the invention can serve as a cosmetic base. Its nutritional provision is considerably advantageous for improvement of the viability, maintenance of the integrity and the balance of the superficial cells of the skin. In particular, it enables the primary intrinsic qualities of the skin to be preserved on a long-lasting basis, its resistance to damage to be increased and, where appropriate, its return to a state of balance to be promoted.

Another subject of the invention is a cosmetic preparation comprising a base defined above, in which the complex nutrient medium constitutes either an active principle, or an excipient in the presence of other active principles which it is capable of potentiating.

The complex nutrient medium of the invention can also be used for the preparation or production of a medicament.

The use of such a medium on a weakened skin (irritated or dehydrated skins, older skins, etc) enables the skin to return to a satisfactory state, in terms both of trophicity and of hydration of the superficial layers of the epidermis.

A medicinal composition comprising a complex nutrient medium according to the invention can serve as a pharmaceutical formulation base, in particular a nutrient pharmaceutical formulation base.

It possesses, in addition, pharmacological properties which will be demonstrated in the examples. According to an advantageous application of a medicinal composition of the invention, it is intended for the preservative treatment of grafts after they are removed. It will preferably take the form of a sterile solution which is especially suitable for the cleaning and maintenance of grafts in third-degree burns victims.

In addition, a composition as defined above has efficacious properties for preventing or treating disorders of cicatrization such as bedsores, varicose ulcers, stretch marks and keloids, and/or a delay of cicatrization.

More generally speaking, a composition according to the invention can be incorporated in any preparation for use in a pharmaceutical formulation, as an active principle optionally with other active principles, but also as an excipient as a result of its capacity to potentiate the action of specific active principles.

The characteristics, applications and advantages of the present invention are described in greater detail in Examples 1 to 4 and FIGS. 1 to 4 below.

Example 1 gives an example of a formulation of a composition of the invention.

Figure 2:
Figure 3:
Figure 3:
Figure 3:

Example 2 demonstrates the properties of a composition of the invention compared to known media, in support of the attached drawing in which:

FIG. 1 is a sectional view of human epidermis after 36 hours of culture in a standard commercial medium designated MCDB 153, marketed, in particular, by IRVINE SCIENTIFIC and GIBCO-BRL, FIG. 2 is a sectional view of human epidermis after 36 hours of culture in a buffered saline solution (PBS), a balanced saline solution commonly used in cell culture, and FIG. 3 is a sectional view of human epidermis cultured in the nutrient medium of the invention, described in Example 1, at different culture times:

A: after 12 hours
B: after 24 hours
C: after 36 hours

Figure 4:
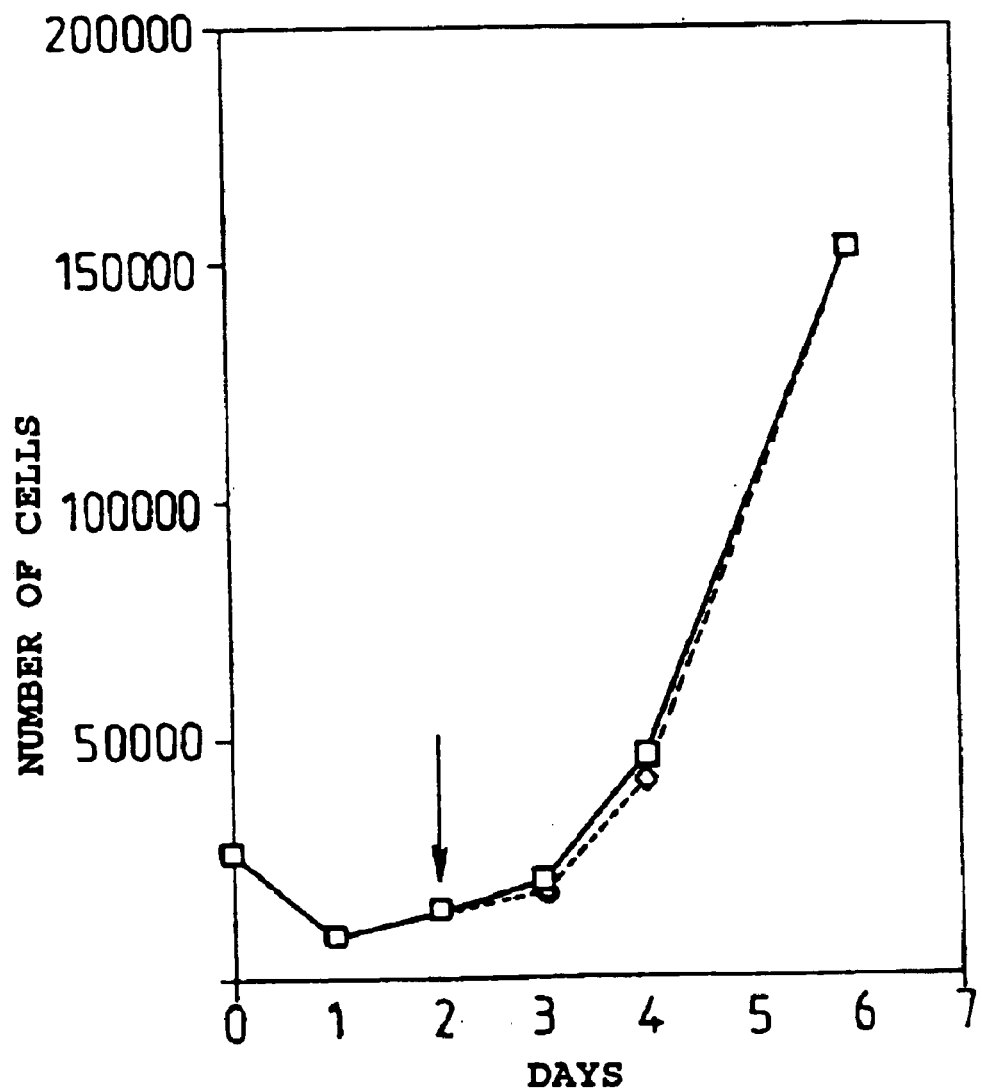

Example 3 demonstrates the absence of stimulation of the proliferation of transformed cells by a composition of the invention compared to a standard composition, in support of FIG. 4 which depicts a diagram showing the multiplication of transformed cells cultured on a medium of the invention and a standard medium.

Example 4 illustrates the pharmacological properties of a composition of the invention: a) on the treatment of grafts; b) on cicatrization.

EXAMPLE 1

Formulation of a composition of the invention

TABLE 1

| COMPONENTS | Concentration in mg/l. |
|---|---|
| Amino acids | |
| L-Alanine | 9.2 |
| L-Arginine HCl | 421.4 |
| L-Asparagine (anhydrous) | 14.2 |
| L-Aspartic acid | 4.0 |
| L-Cysteine HCl.H$_2$O | 42.0 |
| L-Glutamic acid | 14.8 |
| L-Glutamine | 1754.4 |
| Glycine | 7.6 |
| L-Histidine HCl.H$_2$O | 50.0 |
| L-Isoleucine | 6.0 |
| L-Leucine | 131.2 |
| L-Lysine HCl | 54.0 |
| L-Methionine | 13.5 |
| L-Phenylalanine | 10.0 |
| L-Proline | 34.6 |
| L-Serine | 126.1 |
| L-Threonine | 24.0 |
| L-Tryptophan | 9.3 |
| L-Tyrosine 2 Na 2H$_2$O | 11.7 |
| L-Valine | 70.3 |
| Vitamins and organic components | |
| d-Biotin | 0.02 |
| Folic acid | 0.80 |
| Nicotinamide | 0.04 |
| Ca D-Pantothenate | 0.30 |
| Pyridoxine HCl | 0.06 |
| Riboflavin | 0.04 |
| Thiamine HCl | 0.30 |
| Vitamin B$_{12}$ | 0.41 |
| i-Inositol | 18.0 |
| Putrescine 2 HCl | 0.20 |
| Sodium pyruvate | 55.0 |
| Thymidine | 0.73 |

TABLE 1-continued

| COMPONENTS | Concentration in mg/l. |
|---|---|
| Adenine (HCl) | 24.0 |
| DL-Lipoic acid | 0.20 |
| Inorganic components | |
| Sodium chloride | 6800.0 |
| KCl | 112.0 |
| Na$_2$HPO$_4$ | 284.0 |
| CuSO$_4$.5H$_2$O | 0.003 |
| Sodium acetate | 300.0 (anhydrous) |
| D-Glucose | 1080.0 |
| HEPES (piperazine) | 6600.0 |
| Phosphorylethanolamine | 0.06768 |
| Ethanolamine | 0.04684 |
| Sodium sulphate | 3.4 |
| Sodium bicarbonate | 1160.0 |
| FeSO$_4$.7H$_2$O | 1.39 |
| MgCl$_2$.6H$_2$O | 120.0 |
| CaCl$_2$.2H$_2$O | from 13.0 to 22.05 |
| ZnSO$_4$.7H$_2$O | 0.144 |
| (NH4)$_6$MO$_7$O$_{24}$.4H$_2$O | 0.00120 |
| Na$_2$SiO$_3$.5H$_2$O | 0.142 |
| MnCl$_2$.4H$_2$O | 0.00002 |
| SnCl$_2$.2H$_2$O | 0.00011 |
| NH$_4$VO$_3$ | 0.00057 |

EXAMPLE 2

The cytocompatibility and the performance features of the complex nutrient medium described in Example 1 were tested on cultures of human keratinocytes in a monolayer, and on human epidermis reconstituted in vitro.

The nutrient medium according to Example 1 permits the culture of keratinocytes in a monolayer under optimal conditions of viability for at least 36 hours without the slightest cytotoxic effect manifesting itself.

In contrast, a traditional survival solution such as PBS (phosphate buffered saline, a balanced saline solution commonly used in cell culture) proves cytotoxic from 12 hours of incubation onwards.

In agreement with FIG. 3, the nutrient medium according to the example permits culture of normal human epidermis reconstituted under optimal conditions of viability, without cytotoxic manifestations even after 36 hours (FIG. 3C) of contact. The cultures displayed basal, prickle, mast and intact, orthokeratotic cornified cell layers, of regular and normal stratification.

On comparing FIG. 3C with FIG. 1, the latter illustrating the use of a standard commercial medium (MCDB 153, marketed, in particular, by IRVINE SCIENTIFIC), it is seen that the performance features of the medium of the invention are equally good.

In contrast, the use of PBS induces, in agreement with FIG. 2, the appearance of keratinocytes in a terminal phase of differentiation at the level of the basal and prickle strata, with more or less pronounced signs of necrosis. A total detachment of the epidermis is also noted, with complete loss of structuring of the different keratinocytic strata.

EXAMPLE 3

Effects of a composition of the invention on the growth of transformed epidermal cells.

The composition used for this study is the one described in Example 1, comprising the medium termed medium 1.

The effect of the composition 1 on the growth of a spontaneously transformed line of human keratinocytes was tested over 4 days of culture by comparison with cells cultured on a standard medium (DMEM, Dulbeco Modified Epidermal Medium+foetal calf serum).

The cells are first inoculated into the standard medium and grow until the 2nd day after inoculation into this medium. On the 2nd day, the batch of cells is divided into two, one batch continuing to be cultured in standard medium, the other in medium 1.

The results are collated in FIG. 4, in which the curve obtained with the points —☐— corresponds to the composition of the invention and that obtained with the points -☐- corresponds to the composition of standard medium. The points were duplicated and the counts originate from quadruplicates. The results are corrected for the standard error of the mean, SEM. The arrow seen in the diagram corresponds to the dividing of the batch on the second day of culture.

The morphology of the cells differs according to the medium employed. That of the cells cultured in medium 1 resembles more closely that obtained using a semi-defined medium for epithelial cells, of the GIBCO-BRL KSFM type (cells with looser junctions, less pavemental appearance, etc).

No significant difference is noted in the growth of this line in accordance with the different media, up to confluence (days 6 to 7, not shown here).

It is concluded that the composition 1 has no stimulatory effect on the proliferation of transformed keratinocytes.

EXAMPLE 4

Effects of a composition of the invention on the taking of human skin grafts and the prevention of cicatrization disorders.

The composition tested is the one described in Example 1, comprising the medium termed medium 1.

The effects of the composition 1 on the taking of human skin grafts and the prevention of cicatrization disorders were studied on a mouse model (athymic mouse lacking cell-mediated immunity).

Two types of grafts were employed: cultured epidermis and human skins originating from plastic surgery. The grafts were irrigated for 30 days with 1 ml of composition 1 (one application daily) for the group A mice and 1 ml of buffered saline solution (PBS) for the group B mice (20 animals per group). Compresses of tulle gras were applied after each irrigation in order to prevent the grafts from drying out.

A clinical observation of the grafts was carried out on D-7, D-15 and D-30.

Two parameters were evaluated: the necrosis of the cultured epidermis and the cicatrization.

a) the necrosis of the cultured epidermis ("taking of crafts")

Scoring is performed from 0 to 3:0=no sign of necrosis; 1=slight inflammation and superficial degradation of the graft; 2=partial necrosis; 3=total necrosis.

The results are collated in Table 2.

TABLE 2

| Score | D-7 | D-15 | D-30 |
|---|---|---|---|
| GROUP A MICE (20 grafts in total, treated with the nutrient composition) | | | |
| 0 | 9/20 | 12/20 | 16/20 |
| 1 | 7/20 | 4/20 | 0/20 |
| 2 | 3/20 | 2/20 | 2/20 |
| 3 | 1/20 | 2/20 | 2/20 |

TABLE 2-continued

| Score | D-7 | D-15 | D-30 |
|---|---|---|---|
| GROUP B MICE (20 grafts treated with the buffered saline solution) | | | |
| 0 | 2/20 | 4/20 | 7/20 |
| 1 | 8/20 | 6/20 | 3/20 |
| 2 | 6/20 | 5/20 | 5/20 |
| 3 | 4/20 | 5/20 | 5/20 |

The composition 1 improves the taking of the grafts of cultured human epidermis on athymic mice compared to a traditional survival solution (PBS). Significant differences are noted from 7 days of treatment onwards, for a final improvement of more than 50%.

b) the cicatrization (with the crafted whole skins)

Scoring is performed from 0 to 3:0=no cicatrization disorder; 1=delay of cicatrization; 2=delay with abnormality of the cicatrization (granulation of the cicatrix); 3=hypertrophic cicatrix.

The results are collated in Table 3.

TABLE 3

| Score | D-7 | D-15 | D-30 |
|---|---|---|---|
| GROUP A MICE (20 grafted whole skins treated with the nutrient composition) | | | |
| 0 | 20/20 | 16/20 | 15/20 |
| 1 | 0/20 | 3/20 | 2/20 |
| 2 | 0/20 | 1/20 | 2/20 |
| 3 | 0/20 | 0/20 | 1/20 |
| GROUP B MICE (20 grafted whole skins treated with the buffered saline solution) | | | |
| 0 | 16/20 | 10/20 | 5/20 |
| 1 | 4/20 | 7/20 | 8/20 |
| 2 | 0/20 | 3/20 | 3/20 |
| 3 | 0/20 | 0/20 | 4/20 |

The composition 1 significantly improves the cicatrization processes; this effect is especially marked after 30 days of treatment.

What is claimed is:

1. A method of cosmetic treatment, comprising contacting human skin with a treatment composition comprising an aqueous complex nutritive base, wherein said complex nutritive base comprises the following components, the concentration of the components being expressed in milligrams per liter of solvent:

| | |
|---|---|
| L-Alanine | 9.2 |
| L-Arginine HCl | 421.4 |
| L-Asparagine (anhydrous) | 14.2 |
| L-Aspartic acid | 4.0 |
| L-Cysteine HCl.H$_2$O | 42.0 |
| L-Glutamic acid | 14.8 |
| L-Glutamine | 1754.4 |
| Glycine | 7.6 |
| L-Histidine HCl.H$_2$O | 50.0 |
| L-Isoleucine | 6.0 |
| L-Leucine | 131.2 |
| L-Lysine HCl | 54.0 |
| L-Methionine | 13.5 |
| L-Phenylalanine | 10.0 |
| L-Proline | 34.6 |
| L-Serine | 126.1 |
| L-Threonine | 24.0 |

|  |  |
|---|---:|
| L-Tryptophan | 9.3 |
| L-Tyrosine 2 Na 2H$_2$O | 11.7 |
| L-Valine | 70.3 |
| d-Biotin | 0.02 |
| Folic acid | 0.80 |
| Nicotinamide | 0.04 |
| Ca D-Pantothenate | 0.30 |
| Pyridoxine HCl | 0.06 |
| Riboflavin | 0.04 |
| Thiamine HCl | 0.30 |
| Vitamin B$_{12}$ | 0.41 |
| i-Inositol | 18.0 |
| Putrescine 2 HCl | 0.20 |
| Sodium pyruvate | 55.0 |
| Thymidine | 0.73 |
| Adenine (HCl) | 24.0 |
| DL-Lipoic acid | 0.20 |
| D-Glucose | 1080.0 |
| Sodium chloride | 6800.0 |
| KCl | 112.0 |
| Na$_2$HPO$_4$ | 284.0 |
| CuSO$_4$.5H$_2$O | 0.003 |
| Sodium acetate | 300.0 (anhydrous) |
| HEPES (piperazine) | 6600.0 |
| Phosphorylethanolamine | 0.06768 |
| Ethanolamine | 0.04684 |
| Sodium sulphate | 3.4 |
| Sodium bicarbonate | 1160.0 |
| FeSO$_4$.7H$_2$O | 1.39 |
| MgCl$_2$.6H$_2$O | 120.0 |
| CaCl$_2$.2H$_2$O | from 13.0 to 22.05 |
| ZnSO$_4$.7H$_2$O | 0.144 |
| (NH$_4$)$_6$MO$_7$O$_{24}$.4H$_2$O | 0.00120 |
| Na$_2$SiO$_3$.5H$_2$O | 0.142 |
| MnCl$_2$.4H$_2$O | 0.00002 |
| SnCl$_2$.2H$_2$O | 0.00011 |
| NH$_4$VO$_3$ | 0.00057. |

2. A cosmetic composition, comprising an aqueous complex nutritive base comprising the following components, the concentration of the components being expressed in milligrams per liter of solvent:

|  |  |
|---|---:|
| L-Alanine | 9.2 |
| L-Arginine HCl | 421.4 |
| L-Asparagine (anhydrous) | 14.2 |
| L-Aspartic acid | 4.0 |
| L-Cysteine HCl.H$_2$O | 42.0 |
| L-Glutamic acid | 14.8 |
| L-Glutamine | 1754.4 |
| Glycine | 7.6 |
| L-Histidine HCl.H$_2$O | 50.0 |
| L-Isoleucine | 6.0 |
| L-Leucine | 131.2 |
| L-Lysine HCl | 54.0 |
| L-Methionine | 13.5 |
| L-Phenylalanine | 10.0 |
| L-Proline | 34.6 |
| L-Serine | 126.1 |
| L-Threonine | 24.0 |
| L-Tryptophan | 9.3 |
| L-Tyrosine 2 Na 2H$_2$O | 11.7 |
| L-Valine | 70.3 |
| d-Biotin | 0.02 |
| Folic acid | 0.80 |
| Nicotinamide | 0.04 |
| Ca D-Pantothenate | 0.30 |
| Pyridoxine HCl | 0.06 |
| Riboflavin | 0.04 |
| Thiamine HCl | 0.30 |
| Vitamin B$_{12}$ | 0.41 |
| i-Inositol | 18.0 |
| Putrescine 2 HCl | 0.20 |
| Sodium pyruvate | 55.0 |
| Thymidine | 0.73 |
| Adenine (HCl) | 24.0 |
| DL-Lipoic acid | 0.20 |
| D-Glucose | 1080.0 |
| Sodium chloride | 6800.0 |
| KCl | 112.0 |
| Na$_2$HPO$_4$ | 284.0 |
| CuSO$_4$.5H$_2$O | 0.003 |
| Sodium acetate | 300.0 (anhydrous) |
| HEPES (piperazine) | 6600.0 |
| Phosphorylethanolamine | 0.06768 |
| Ethanolamine | 0.04684 |
| Sodium sulphate | 3.4 |
| Sodium bicarbonate | 1160.0 |
| FeSO$_4$.7H$_2$O | 1.39 |
| MgCl$_2$.6H$_2$O | 120.0 |
| CaCl$_2$.2H$_2$O | from 13.0 to 22.05 |
| ZnSO$_4$.7H$_2$O | 0.144 |
| (NH$_4$)$_6$MO$_7$O$_{24}$.4H$_2$O | 0.00120 |
| Na$_2$SiO$_3$.5H$_2$O | 0.142 |
| MnCl$_2$.4H$_2$O | 0.00002 |
| SnCl$_2$.2H$_2$O | 0.00011 |
| NH$_4$VO$_3$ | 0.00057. |

\* \* \* \* \*